(12) United States Patent
Blin et al.

(10) Patent No.: US 7,110,508 B2
(45) Date of Patent: Sep. 19, 2006

(54) FILTER FOR A RADIATION EMITTER AND APPARATUS

(75) Inventors: Philippe Blin, Maurepas (FR); Xavier Le Pennec, Trappes (FR); Marta Diez Torca, Paris (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/937,452

(22) Filed: Sep. 9, 2004

(65) Prior Publication Data

US 2005/0058255 A1  Mar. 17, 2005

(30) Foreign Application Priority Data

Sep. 12, 2003  (FR) .................................. 03 50534

(51) Int. Cl.
  *G21K 3/00*   (2006.01)
(52) U.S. Cl. ........................................ 378/156; 378/145
(58) Field of Classification Search .................. 378/37, 378/156, 157, 158, 145
See application file for complete search history.

(56) References Cited

U.S. PATENT DOCUMENTS

| 4,219,734 A | 8/1980 | Chery ........................ 378/24 |
| 6,633,627 B1 * | 10/2003 | Horiuchi ..................... 378/156 |
| 2003/0199757 A1 * | 10/2003 | Toth et al. .................. 600/425 |

FOREIGN PATENT DOCUMENTS

| EP | 0 629 377 A | 12/1994 |
| EP | 982 002 A | 3/2000 |
| EP | 1 120 086 A | 8/2001 |

* cited by examiner

*Primary Examiner*—Courtney Thomas
(74) *Attorney, Agent, or Firm*—Cantor Colburn, LLP

(57) ABSTRACT

A filter plate having defects that may cause image artefacts is moved during an exposure. The movement distributes the defects of the plate in the image to a point where they can no longer be seen in the image. Preferably, the shifting of the plate is done in the plane of the plate, in a direction perpendicular to the axes of the rollers used for in the manufacture of the plate.

36 Claims, 2 Drawing Sheets

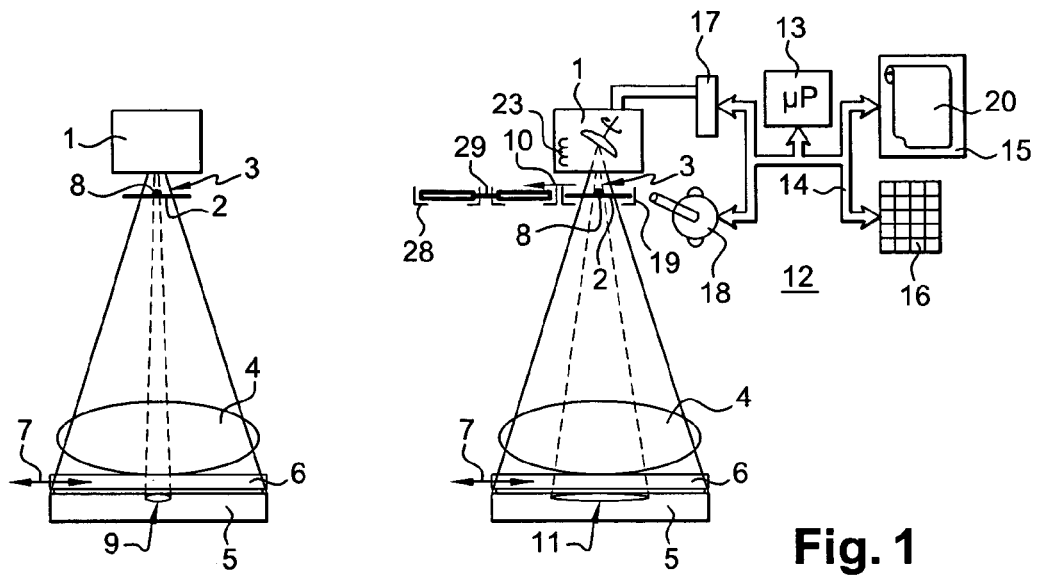
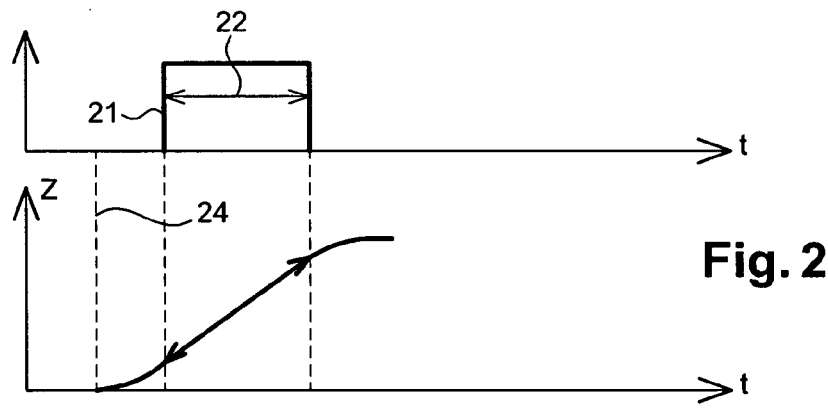
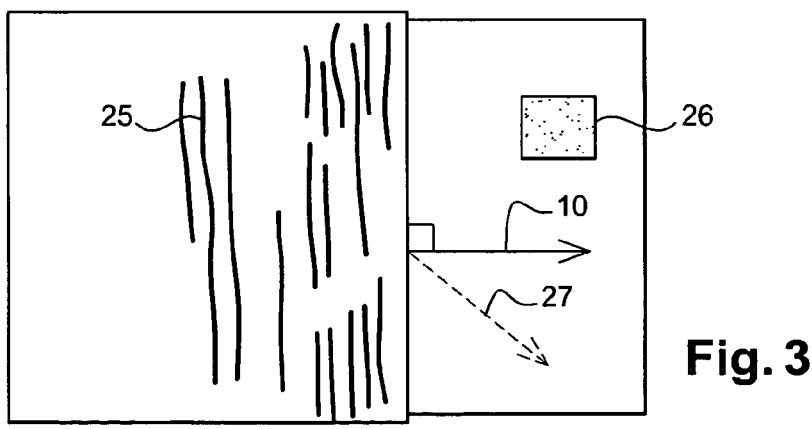
Fig. 1
Fig. 2
Fig. 3

FILTER FOR A RADIATION EMITTER AND APPARATUS

CROSS-REFERENCE TO RELATED APPLICATIONS

This application claims the benefit of a priority under 35 USC 119(a)–(d) to French patent application No. 03 50534 filed Sep. 12, 2003, the entire contents of which are hereby incorporated by reference.

BACKGROUND OF THE INVENTION

An embodiment of the present invention is directed to a radiation emitter and in particular to an emitter of X-ray radiation. An embodiment of the present invention is also directed to a radiology apparatus that may include a radiation emitter and in particular an apparatus that can be used in medical imaging for example, for imaging an object. More particularly, an embodiment of the invention is directed to an apparatus for mammography. The embodiments of the present invention, however, can be applied to any other field in which radiography or a radiological examination is undertaken, to include by way of example, CT, vascular, Rad-R&F.

A conventional radiology apparatus comprises means for providing emitted radiation, such as an X-ray tube emitting X-rays. The emitted radiation is directed toward a body to be examined. The body may be any object for which a generally non-destructive investigation by imaging of the internal structure of the object is desired, such as a casting formed by metal and non-metal materials. In medical imaging, the body to be examined may be a patient's body. On another side of this body, relative to the tube, there is a detector. In practice, the detector is typically a radiographic film or an electronic detector, for example of the type with a radiology image intensifier screen.

When applied to medical imaging, depending on the nature of the lesions or structures to be revealed, there are known ways of choosing the hardness of the X-rays emitted as well as, for reasons of detection threshold, the emission power. The rays thus emitted cross the body and excite the detector in revealing the attenuation that they undergo at certain places. The problems that disturb this type of detection are of different kinds.

In particular, there are known problems of scattering in which certain parts of the body stop the emitted X-rays, without absorbing them, and become the site of Compton scattering. The rays that result from this scattering themselves also go through the rest of the body and excite the detector but, unfortunately, they do so at a place which is not straight ahead of the structure which is the site of their emission. The image is then falsified. To prevent this type of defect, there are known ways of collimating the rays by means of a grid screen which, on the whole, lets through only X-rays having a planned orientation (generally a perpendicular orientation) relative to the detector. However, to prevent traces of the grid screen from being seen in the revealed image, there are known ways of shifting the grid screen during examination. Consequently, the traces of this grid screen are distributed in the image to the point of becoming invisible.

Mammography presents a problem that is more difficult than perhaps in other radiological imaging. In mammography (but can be seen in other fields) the difficulty is related to the low level of differentiation of absorption between the healthy tissues of a breast and tissues affected by lesions, especially instances of microcalcification. To resolve this problem, X-ray emission filters that confine the spectrum of the emitted X-rays to the narrowest possible spectrum are used. The spectrum is at a value of hardness such that the rays emitted are highly absorbed by the healthy structures and less absorbed by the unhealthy structures (or vice versa) so that the contrast of the image is increased.

The production of the X-rays is obtained by the projection, at very high speeds, of electrons emitted by a cathode on an anode of the tube. Despite the choice of targets of the anode made out of appropriate materials, the spectrum of emission of the X-rays has an excessively great bandwidth. It may happen in this case that the structure to be revealed, which would have blocked rays at a given frequency, lets through rays at another frequency and the reverse would happen for other structures. This results in a loss of contrast. This is why it is desirable to filter the emission produced so as to confine the spectrum to a narrow band.

The means for filtering comprises a plate, which is generally a metal plate, interposed between the X-ray tube and the body. Thus, the interposing of a plate made of molybdenum, rhodium, aluminium, copper, gold or silver may, as the case may be, enable the choice of the range of X-rays to be used.

However, the interposing of the plate itself poses a problem. This problem is related to defects arising from the manner of manufacture of the plate, which is often obtained by rolling. The defects, which are visible in very precise conditions of examination, especially with a homogeneous interposed body (during the calibration) and with x-radiation confined in a narrow spectrum, take the form of spots or lines. In the latter case especially, the defects often have a pronounced direction that is of the axes of the rollers. Defects of this type are especially present in rhodium type filters.

The variations of attenuation of the plate may also have several other possible reasons such as the local liberation of material from the surface, local variations in thickness or variations in density.

A way to reveal these defects is a technique of contrast expansion, performed during tests of homogeneity, in a narrow window of brightness of the detected signal. The filter plates generally have a thickness of 25 to 30 micrometers.

In X-ray mammography imaging it is sought to obtain very small differences in contrast created by clinical signs such as microcalcification or masses. These biological tissues have a very low difference in coefficient of radiological transmission with the tissues whose place they take. Consequently, the spatial homogeneity of the filter must be very high. For example, it has been recognized that a local variation in attenuation, in the range of 2.5% around the nominal value of 25 to 30 micrometers, makes the images unusable. Ultimately, improved homogeneity must be acquired throughout the surface of the filter plates.

BRIEF DESCRIPTION OF THE INVENTION

An embodiment of the invention seeks to overcome one or more of the above problems by providing a shift in the filter at the time of the exposure, preferably in parallel to its plane, so as to distribute the contribution of the defects that it causes in the image. This contribution is distributed over a wider surface. In this way, the amplitudes of the artefacts thus formed are themselves reduced to the point where they become smaller than the lesion-revealing differences in contrast to be observed.

An embodiment of the invention is a radiology apparatus comprising means for emitting radiation, such as an X-ray emitter tube and means for filtering, such as a plate for the filtering of the emitted radiation. The means for filtering can be located in an intermediate position between the means for emitting radiation and a body to be subjected to the emitted radiation. The apparatus comprises means to control a radiation emission for the duration of a radiology exposure and means to move the filter for the duration of the exposure.

BRIEF DESCRIPTION OF THE DRAWINGS

The embodiments of the invention will be better understood from the following description and the accompanying figures. These figures are given purely by way of an indication and in no way restrict the scope of the invention. In the figures:

FIG. 1 is a schematic view of a radiology apparatus respectively before and after the implementation of an embodiment of the invention;

FIG. 2 is a timing diagram showing the development of the position of the means for filtering during an exposure;

FIG. 3 is a view of images obtained in the presence of an interposed body that is homogeneous.

DETAILED DESCRIPTION OF THE INVENTION

Figure 4:
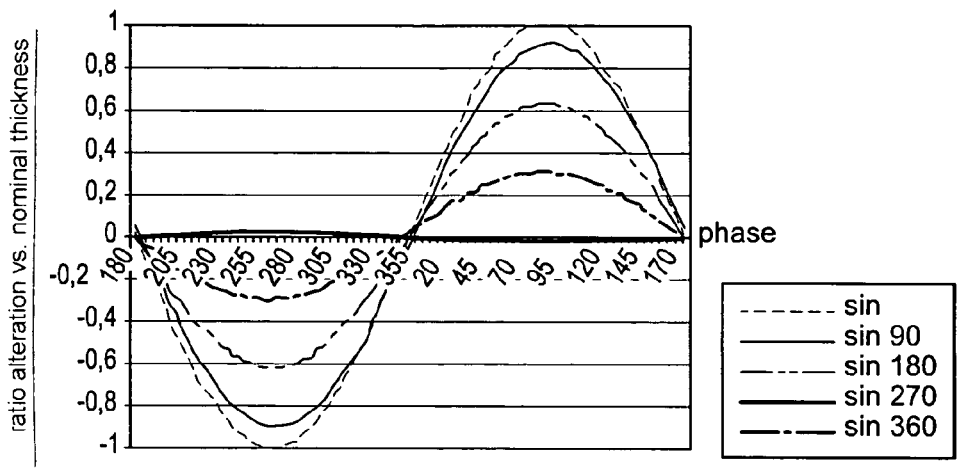
FIGS. 4 to 6 shows developments of contributions of defects as a function of different ways of putting the means for filter into motion.

FIG. 1 presents two views, one to the left and one to the right, of a radiology apparatus respectively before and after the implementation of an embodiment of the invention. The radiology apparatus comprises means for emitting radiation, such as an X-ray tube 1 and means for filtering the emitted radiation, such as a plate 2 for the filtering of the X-rays 3 emitted by the tube 1. The plate 2 is located in an intermediate position between the tube 1 and an object to be imaged, such as body 4, in particular a body of a patient to be examined and which is subjected to radiation from tube 1. On the other side of the body 4 relative to the tube 1, is a means 5 for detecting the radiation after the radiation has passed through the object. The means 5 is surmounted, in a manner that is known in radiography, by a moving antiscatter grid screen 6 that can shift along arrows showing alternating directions 7. In the prior art, as seen in the left-hand figure, a defect 8 of the means 2 results in a very pronounced spot 9 (of high contrast) which is furthermore of a small size.

During exposure or imaging, the means 2 is shifted, for example in the direction of arrow 10 and generally parallel to its plane and perpendicular to the radiation 3. As a result of the movement of means 2, the image of the defect 8 is distributed over a surface 11 that is far greater. As a consequence, the contrast of the spot is far less pronounced.

The apparatus comprises means 12 to control the emission from the means 1 for emitting radiation. The means 12 comprises a microprocessor 13 linked by a bus 14 with a program memory 15, a data memory 16, an input/output interface 17 and in an embodiment, means 18 for driving (shown in a schematic view). The means 18 for driving is used to put the means 2 for filtering into motion. The means 18 for driving, may comprise a micromotor interposed between a side of a support of the means 2 and an edge 19 of the means 2 and may furthermore comprise piezoelectric or electromagnetic elements. For example, the edge 19 of the means 2 can be provided with a magnetized tape. This tape is subjected to the influence of an electromagnetic pole delivering a field with an amplitude that varies alternately in time.

A program 20 contained in the memory 15 comprises for example means to excite the motor 18 (or the like) at a point in time 24 shortly before the start 21 of the duration 22 of a radiology exposure undertaken with the apparatus. For example, the duration 22 and the instant 21 are dictated by the microprocessor 13 that places one or more voltage square waves, liable to suitably excite the cathode 23 of the tube 1, on the interface 17. Since the speed of shift of the plate 2 is zero at the outset, the placing of the means 2 in motion in the direction 10 of the means 2 is anticipated at a date 24, so that, during the period 22, the speed at which the means 2 is shifted has a perfectly linear shape. By acting in this way, it is ensured that the contribution of the defect 8 will be carried out uniformly throughout the surface 11 and will therefore be reduced in proportion to the size of this spot.

FIG. 3 shows different types of defects. The left-hand part of the figure in particular shows traces of rolling 25 presenting an elongated appearance in the plane of the means 2, all these traces being parallel to each other. The defects thus brought about can subsequently be likened to a sine variation whose spatial wavelength is equal to the distance between two contiguous traces. In the right-hand parts of FIG. 3, in a designation square 26, is an indication of an isolated spot having a (very slightly) lighter color.

The direction of the motion 10 to which the plate 3 is subjected is, in the case of the rolling traces 25, preferably perpendicular to the direction of elongation of these traces 25. If, as happens sometimes, the plate has been obtained by a crossed double rolling process, then other rolling traces are seen to appear in a direction perpendicular to the direction 25. These traces are elongated in directions perpendicular to the directions 25. In this case, the direction 10 of shift of the plate 2 will be oriented along the direction 27 that is substantially a bisector of the angle formed by the two directions of the rolling alignments such as 25. When the two directions are at 90° to each other, the direction 27 is approximately at 45°.

Figure 5:
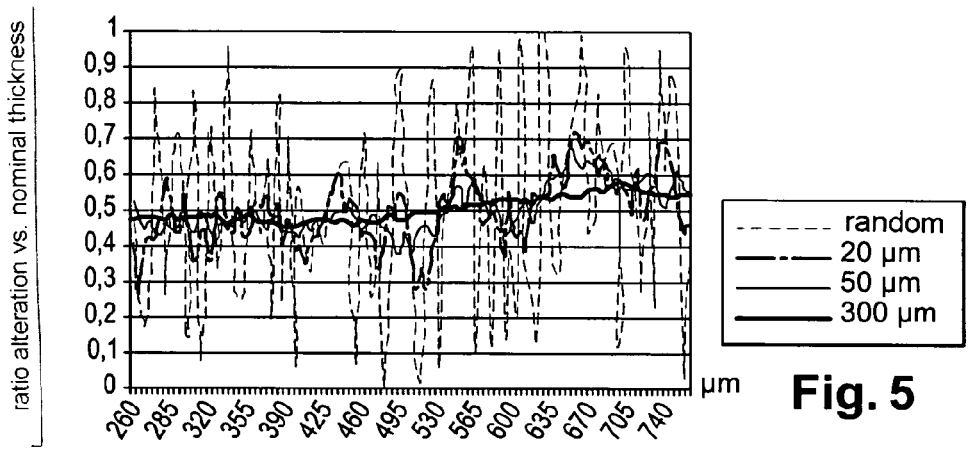
Figure 6:
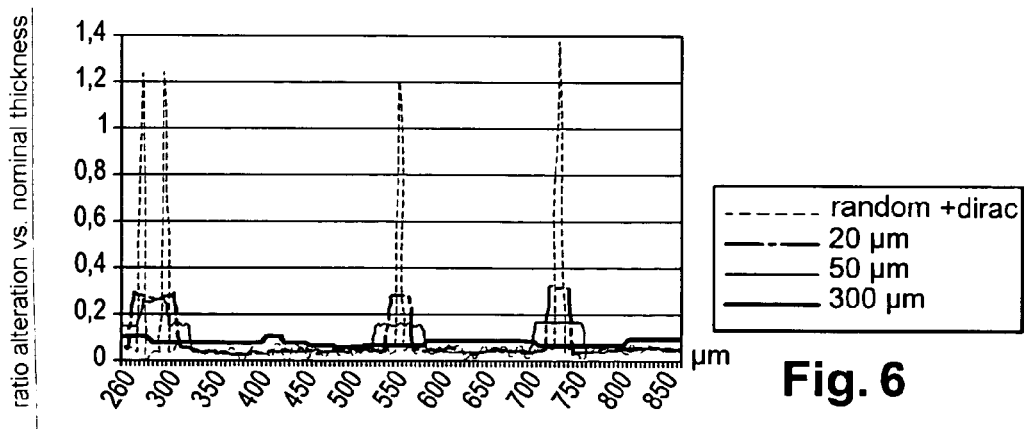

FIGS. 4 to 6 show the length of shift of the plate 2. In FIG. 4, it is shown that for a defect of the type 25 with a density profile that is substantially sinusoidal (in the direction 10), it is possible to make a shift that is equal to a quarter, half or three-quarters of the length of the sine wave thus detected, or equal to the full wavelength thus detected. If the shift is about a quarter of the wavelength, the amplitudes of the artefacts are reduced by only 10%. If the length of the shift is about half the wavelength, the contribution of the artefact is reduced by about 40%. The contribution is reduced by 70% if the length of the shift is about three-quarters of the wavelength. It is reduced by almost 100% when the length of the shift is equal to the wavelength.

In FIG. 5, if the contribution of the defects is random in the profile, for defects whose mean wavelength is in the range of 20 to 30 micrometers, their contribution in the image is reduced, in terms of peak value, by 60% when the exploration of the shift is in the same range as this mean wavelength, namely 20 micrometers. This contribution remains still significant, although well attenuated, when the shift is greater than or equal to twice this mean wavelength. However, this contribution is highly attenuated when the shift is greater than or equal to 15 times the mean wavelength of the defects. For shifts in the range of 300 micrometers, the contribution of the defects remains always lower than 10%.

FIG. 6 gives a view, under the same conditions, of the spread effect resulting from the shift of the plate 2 for highly accentuated local defects. For random and isolated defects, the shift of about 300 micrometers, for example at least 250 micrometers, and of over 300 micrometer, is sufficient to make the artefacts caused by the manufacture of the plates to disappear significantly (with a remanence of less than 10%).

Instead of shifting the plate 2 by means 18, it is possible to use the presence, in a radiology apparatus, of a turntable or carrousel. Such a turntable can used to present either of the chosen plates before the tube 1 in order to carry out an expected radiology examination. Such a turntable comprises a set of cradles such as 28 linked to one another in a continuous circle by a conveyance structure 29. In this case, rather than add as means for driving, such as motor 18, it is sufficient to continue mobilizing the conveyance means 29 and continue to move the turntable during the exposure so as to distribute the defects of the plates. Whatever is the chosen means for driving, the microprocessor 13 implementing the program 20 will drive the means for putting the plate 2 into motion so that the movement remains substantially linear as can be seen in FIG. 2.

One skilled in the art may make or propose various modifications in the structure and/or way and/or function and/or result of the disclosed embodiments without departing from the scope and extant of the disclosed embodiments and equivalents thereof.

What is claimed is:

1. A radiology apparatus comprising:
   means for emitting radiation;
   means for filtering the emitted radiation being located in an intermediate position between the means for emitting radiation and a body to be subjected to the emitted;
   means for controlling an emission of the means for emitting radiation for a duration of a radiology exposure; and
   means for moving the means for filtering for the duration of the exposure;
   wherein in response to the means for filtering having a defect, the means for moving causes the means for filtering to shift in a manner that reduces the intensity of an image artifact arising from the defect in the means for filtering.

2. The apparatus according to claim 1 wherein the means for filtering is a plate.

3. The apparatus according to claim 1 wherein the means for moving the filter comprise means for causing the rate of movement to be linear during the exposure.

4. The apparatus according to claim 2 wherein the means for moving the filter comprise means for causing the rate of movement to be linear during the exposure.

5. The apparatus according to claim 1 wherein the means for moving comprise means for causing the movement of the means for filtering to be oriented at approximately 90° relative to alignment of elongated patterns present on the means for filtering.

6. The apparatus according to claim 2 wherein the means for moving comprise means for causing the movement of the means for filtering to be oriented at approximately 90° relative to alignment of elongated patterns present on the means for filtering.

7. The apparatus according to claim 3 wherein the means for moving comprise means for causing the movement of the means for filtering to be oriented at approximately 90° relative to alignment of elongated patterns present on the means for filtering.

8. The apparatus according to claim 4 wherein the means for moving comprise means for causing the movement of the means for filtering to be oriented at approximately 90° relative to alignment of elongated patterns present on the means for filtering.

9. The apparatus according to claim 1 wherein the means for moving comprise means for causing the movement of the means for filtering to be oriented at approximately 45° relative to alignment of elongated patterns present on the means for filtering.

10. The apparatus according to claim 2 wherein the means for moving comprise means for causing the movement of the means for filtering to be oriented at approximately 45° relative to alignment of elongated patterns present on the means for filtering.

11. The apparatus according to claim 3 wherein the means for moving comprise means for causing the movement of the means for filtering to be oriented at approximately 45° relative to alignment of elongated patterns present on the means for filtering.

12. The apparatus according to claim 4 wherein the means for moving comprise means for causing the movement of the means for filtering to be oriented at approximately 45° relative to alignment of elongated patterns present on the means for filtering.

13. The apparatus according to claim 5 wherein:
   the elongated patterns comprise consecutive elongated patterns having a defined sine variation with a spatial wavelength equal to the distance between two consecutive elongated patterns; and
   the means for moving comprise means for causing the movement of the means for filtering to have a length greater than the spatial wavelength of the elongated patterns.

14. The apparatus according to claim 6 wherein:
   the elongated patterns comprise consecutive elongated patterns having a defined sine variation with a spatial wavelength equal to the distance between two consecutive elongated patterns; and
   the means for moving comprise means for causing the movement of the means for filtering to have a length greater than the spatial wavelength of the elongated patterns.

15. The apparatus according to claim 7 wherein:
   the elongated patterns comprise consecutive elongated patterns having a defined sine variation with a spatial wavelength equal to the distance between two consecutive elongated patterns; and
   the means for moving comprise means for causing the movement of the means for filtering to have a length greater than the spatial wavelength of the elongated patterns.

16. The apparatus according to claim 8 wherein;
   the elongated patterns comprise consecutive elongated patterns having a defined sine variation with a spatial wavelength equal to the distance between two consecutive elongated patterns; and
   the means for moving comprise means for causing the movement of the means for filtering to have a length greater than the spatial wavelength of the elongated patterns.

17. The apparatus according to claim 9 wherein:
   the elongated patterns comprise consecutive elongated patterns having a defined sine variation with a spatial wavelength equal to the distance between two consecutive elongated patterns; and the means for moving comprise means for causing the movement of the means for filtering to have a length greater than the spatial wavelength of the elongated patterns.

18. The apparatus according to claim 10 wherein:

the elongated patterns comprise consecutive elongated patterns having a defined sine variation with a spatial wavelength equal to the distance between two consecutive elongated patterns; and the means for moving comprise means for causing the movement of the means for filtering to have a length greater than the spatial wavelength of the elongated patterns.

19. The apparatus according to claim 11 wherein:

the elongated patterns comprise consecutive elongated patterns having a defined sine variation with a spatial wavelength equal to the distance between two consecutive elongated patterns; and the means for moving comprise means for causing the movement of the means for filtering to have a length greater than the spatial wavelength of the elongated patterns.

20. The apparatus according to claim 12 wherein:

the elongated patterns comprise consecutive elongated patterns having a defined sine variation with a spatial wavelength equal to the distance between two consecutive elongated patterns; and the means for moving comprise means for causing the movement of the means for filtering to have a length greater than the spatial wavelength of the elongated patterns.

21. The apparatus according to claim 1 wherein the means for moving the means for filtering comprise means for causing the movement of the means for filtering to have a length greater than 300 micrometers.

22. The apparatus according to claim 1 wherein the movement of the means for filtering is controlled with respect to a pattern of defects on the means for filtering.

23. The apparatus according to claim 22 wherein the pattern approximates a sine wave.

24. The apparatus according to claim 1 wherein the means for moving the means for filtering comprise micrometers or piezoelectric elements.

25. The apparatus according to claim 1 wherein the means for moving the means for filtering comprise means for positioning the means for filtering before the means for emitting radiation.

26. The apparatus according to claim 25 wherein the means for positioning comprises a turntable.

27. The apparatus according to claim 1 wherein the means for filtering is made of rhodium, molybdenum, aluminium, copper, gold or silver.

28. The apparatus according to claim 1 wherein the means for moving the means for filtering comprise means for steering the movement of the means for filtering.

29. The apparatus according to claim 1, wherein:

the apparatus is a mammography apparatus.

30. The apparatus according to claim 1, wherein the means for moving comprise means for causing the movement of the means for filtering to be oriented at an angle equal to or greater than 45° and equal to or less than 90° relative to alignment of elongated patterns present on the means for filtering.

31. The apparatus according to claim 26, wherein the means for moving comprises means for continually moving the turntable during the exposure.

32. An installation comprising:

means for filtering emitted radiation;

means for controlling an emission of the means for emitting radiation for a duration of a radiology exposure; and means for moving the means for filtering for the duration of the exposure;

wherein in response to the means for filtering having a defect, the means for moving causes the means for filtering to shift in a manner that reduces the intensity of an image artifact arising from the defect in the means for filtering.

33. The installation according to claim 32 wherein the movement of the means for filtering is controlled with respect to a pattern of defects on the means for filtering.

34. The installation according to claim 32 wherein the movement of the means for filtering is oriented with respect to a pattern of defects on the means for filtering.

35. The installation according to claim 33 wherein the movement of the means for filtering is oriented with respect to a pattern of defects on the means for filtering.

36. The installation according to claim 32, wherein:

the installation comprises a mammography apparatus.

* * * * *